US011510653B2

(12) United States Patent
Shimizu et al.

(10) Patent No.: US 11,510,653 B2
(45) Date of Patent: Nov. 29, 2022

(54) SECONDARY FLOW DETECTION DEVICE, SECONDARY FLOW DETECTION PROGRAM, AND ULTRASONIC SIGNAL PROCESSING DEVICE

(71) Applicant: Hitachi, Ltd., Tokyo (JP)

(72) Inventors: Motochika Shimizu, Tokyo (JP); Takashi Okada, Tokyo (JP); Tomohide Nishiyama, Tokyo (JP)

(73) Assignee: FUJIFILM Healthcare Corporation, Kashiwa (JP)

( * ) Notice: Subject to any disclaimer, the term of this patent is extended or adjusted under 35 U.S.C. 154(b) by 131 days.

(21) Appl. No.: 16/742,333

(22) Filed: Jan. 14, 2020

(65) Prior Publication Data

US 2020/0281569 A1 Sep. 10, 2020

(30) Foreign Application Priority Data

Mar. 8, 2019 (JP) ............................. JP2019-042802

(51) Int. Cl.
*A61B 8/08* (2006.01)
*A61B 8/06* (2006.01)
(Continued)

(52) U.S. Cl.
CPC ................ *A61B 8/488* (2013.01); *A61B 8/06* (2013.01); *A61B 8/0883* (2013.01);
(Continued)

(58) Field of Classification Search
CPC ......... A61B 8/488; A61B 8/06; A61B 8/0883; A61B 8/461; A61B 8/4488; A61B 8/5207;
(Continued)

(56) References Cited

U.S. PATENT DOCUMENTS

2008/0269611 A1* 10/2008 Pedrizzetti ............... A61B 8/06
600/454
2012/0265075 A1* 10/2012 Pedrizzetti ............ G06T 11/206
600/454
(Continued)

FOREIGN PATENT DOCUMENTS

JP 2015-188736 A 11/2015

OTHER PUBLICATIONS

"Material transport in the left ventricle with aortic valve regurgitation", Giuseppe Di Labbio, Jérôme Vétel, and Lyes Kadem Phys. Rev. Fluids 3, 113101—Published Nov. 16, 2018; Erratum Phys. Rev. Fluids 6, 059901 (2021) (Year: 2018).*

*Primary Examiner* — Sean D Mattson
*Assistant Examiner* — Michael Yiming Fang
(74) *Attorney, Agent, or Firm* — Crowell & Moring LLP

(57) ABSTRACT

To uniformly extract a secondary flow based on quantitative calculation even in a complicated blood flow in a heart chamber or a blood vessel. There is provided a secondary flow detection device, including: a degree-of-swirl map calculation unit that obtains a velocity vector map calculated based on an echo signal reflected by an inspection target, calculates, as a value indicating a degree of a spatial change of a velocity vector, a degree of swirl based on the velocity vector map, and calculates, as a degree-of-swirl map, a spatial distribution of an iso-degree-of-swirl line obtained by connecting the degree of swirl of an equal value; a secondary flow candidate extraction unit that extracts, as a secondary flow candidate, an iso-degree-of-swirl line satisfying a predetermined condition among the iso-degree-of-swirl line indicated in the degree-of-swirl map; a feature amount calculation unit that calculates a feature amount of the velocity vector inside the secondary flow candidate; a secondary flow determination unit that determines whether the secondary flow candidate is a desired secondary flow based (Continued)

on the feature amount; and a secondary flow extraction unit that extracts and outputs the secondary flow determined by the secondary flow determination unit.

17 Claims, 20 Drawing Sheets

(51) Int. Cl.
*A61B 8/00* (2006.01)
*G01S 15/89* (2006.01)
(52) U.S. Cl.
CPC ............ *A61B 8/4488* (2013.01); *A61B 8/461* (2013.01); *A61B 8/5207* (2013.01); *A61B 8/5223* (2013.01); *A61B 8/54* (2013.01); *G01S 15/8984* (2013.01)
(58) Field of Classification Search
CPC ........... A61B 8/5223; A61B 8/54; A61B 8/00; G01S 15/8984
See application file for complete search history.

(56) References Cited

U.S. PATENT DOCUMENTS

| | | | | |
|---|---|---|---|---|
| 2013/0296703 | A1* | 11/2013 | Wei | A61B 8/06 600/441 |
| 2015/0094584 | A1* | 4/2015 | Abe | A61B 8/5223 600/443 |
| 2016/0361040 | A1* | 12/2016 | Tanaka | A61B 8/5246 |
| 2017/0105699 | A1* | 4/2017 | Miyaji | A61B 8/5207 |

* cited by examiner

[FIG. 1]
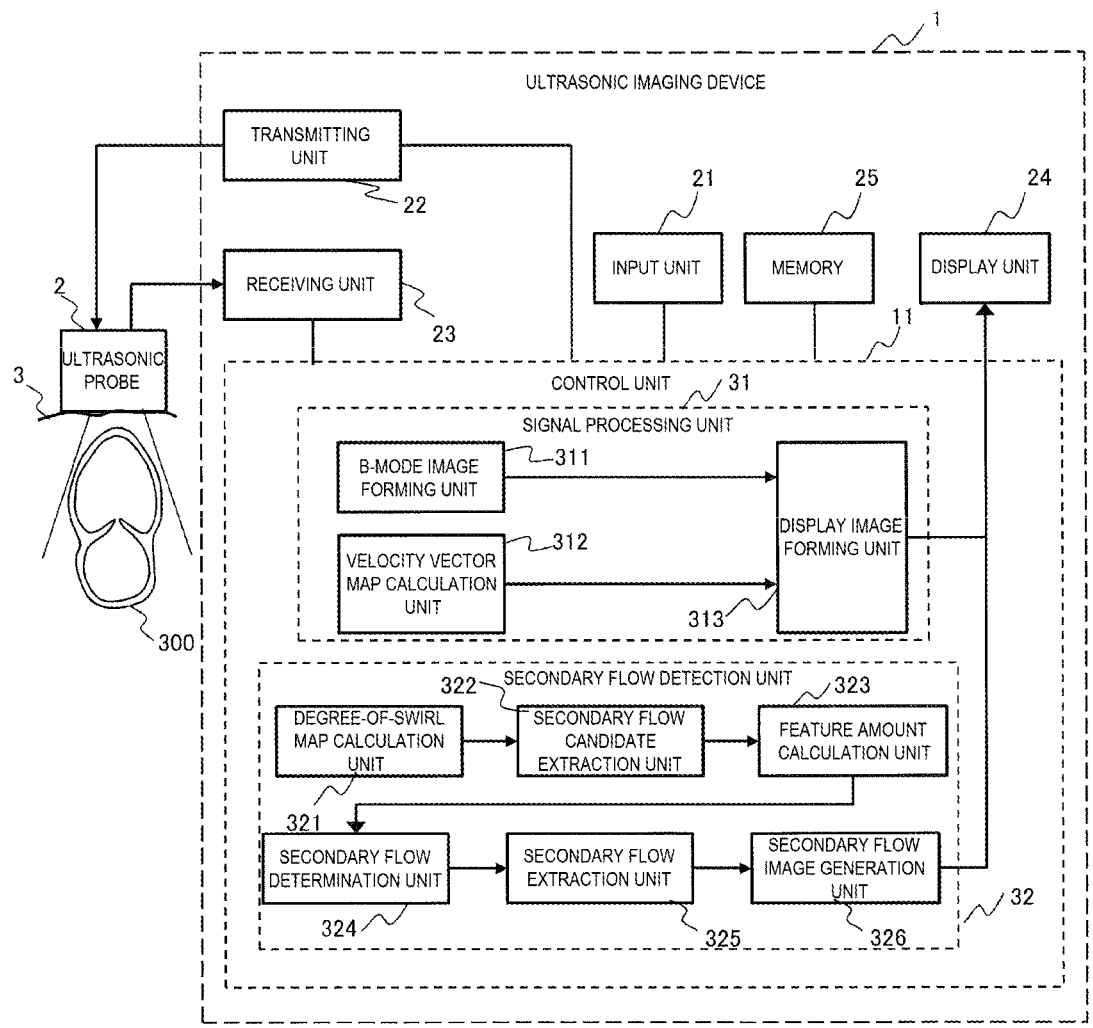

[FIG. 2]
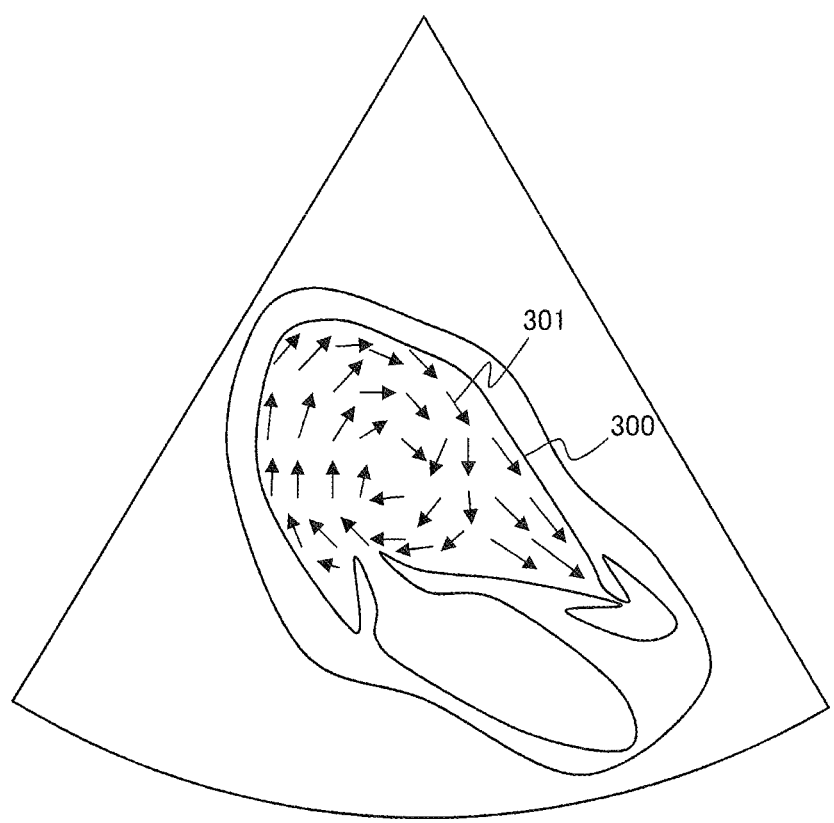

[FIG. 3]
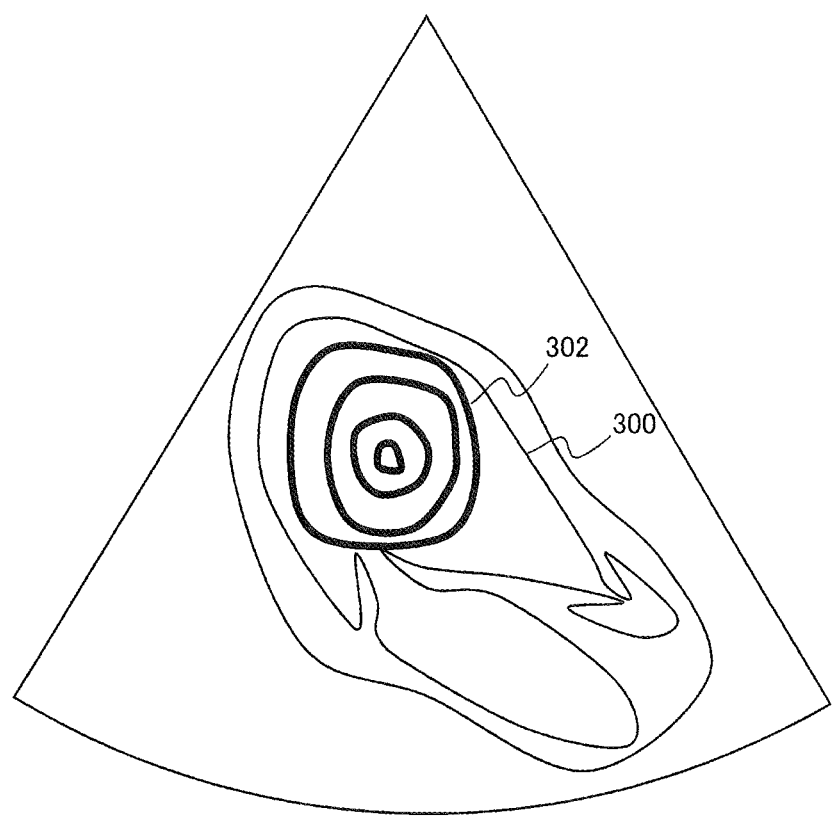

[FIG. 4]
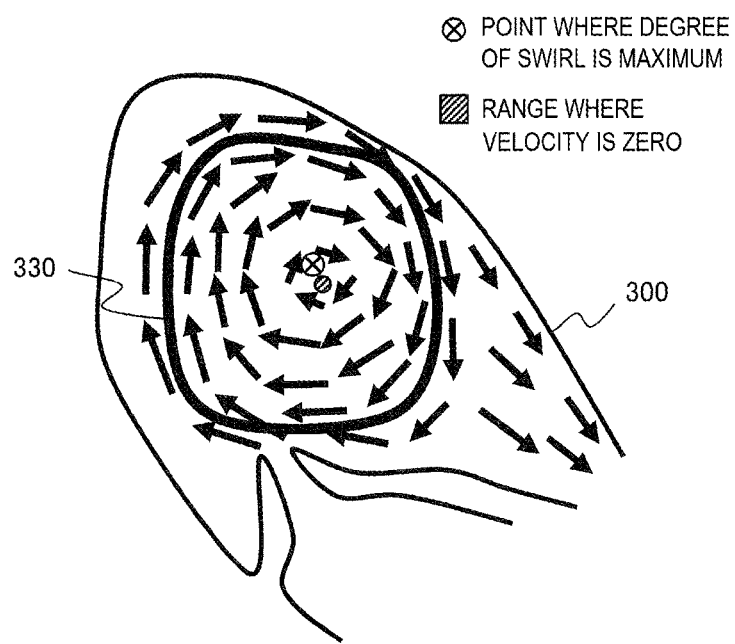

[FIG. 5]
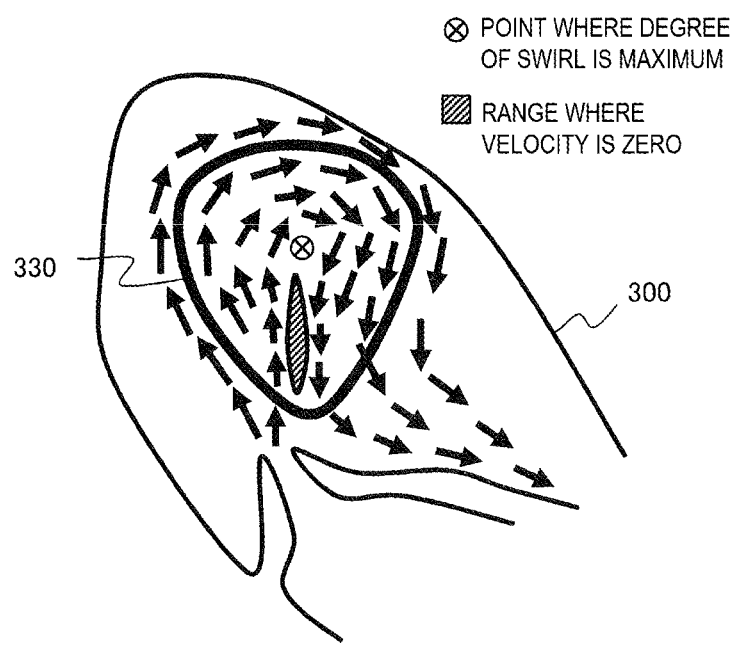

[FIG. 6]
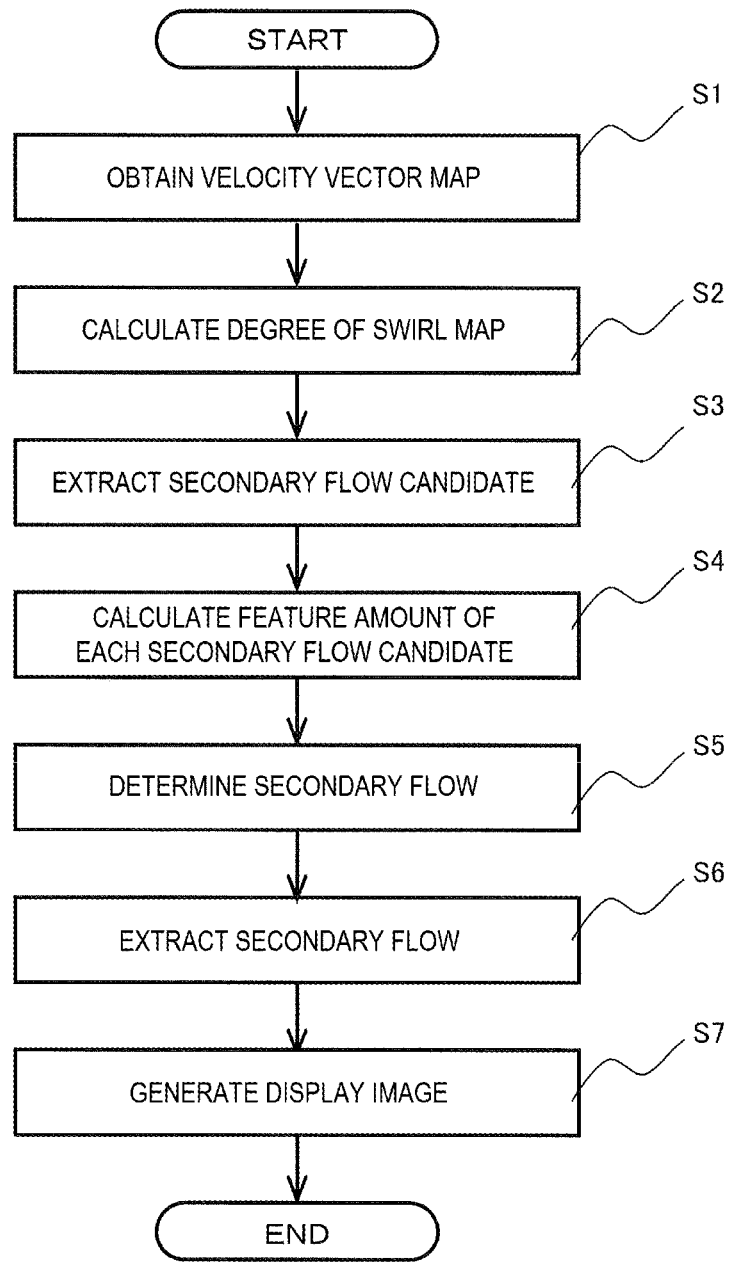

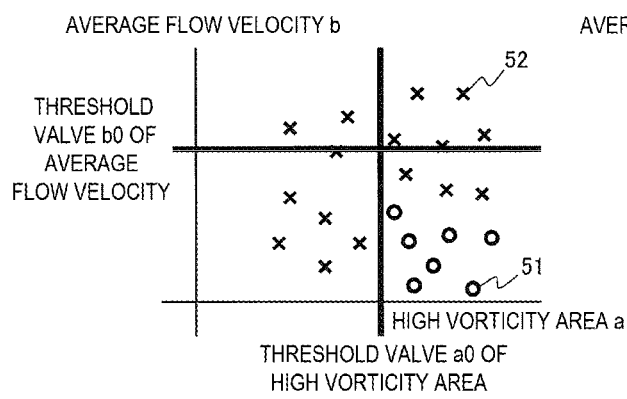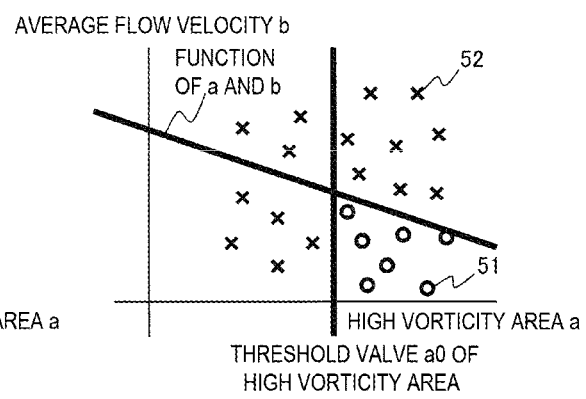

[FIG. 9]

|  | HIGH VORTICITY AREA a | AVERAGE FLOW VELOCITY b | LOW VELOCITY AREA c | MINIMUM FLOW VELOCITY d |
|---|---|---|---|---|
| CANDIDATE 1 | 0.90 | 10 | 0.10 | 5 |
| CANDIDATE 2 | 0.80 | 35 | 0.05 | 10 |
| CANDIDATE 3 | 0.85 | 40 | 0.15 | 15 |
| CANDIDATE 4 | 0.55 | 32 | 0.10 | 15 |

[FIG. 10]
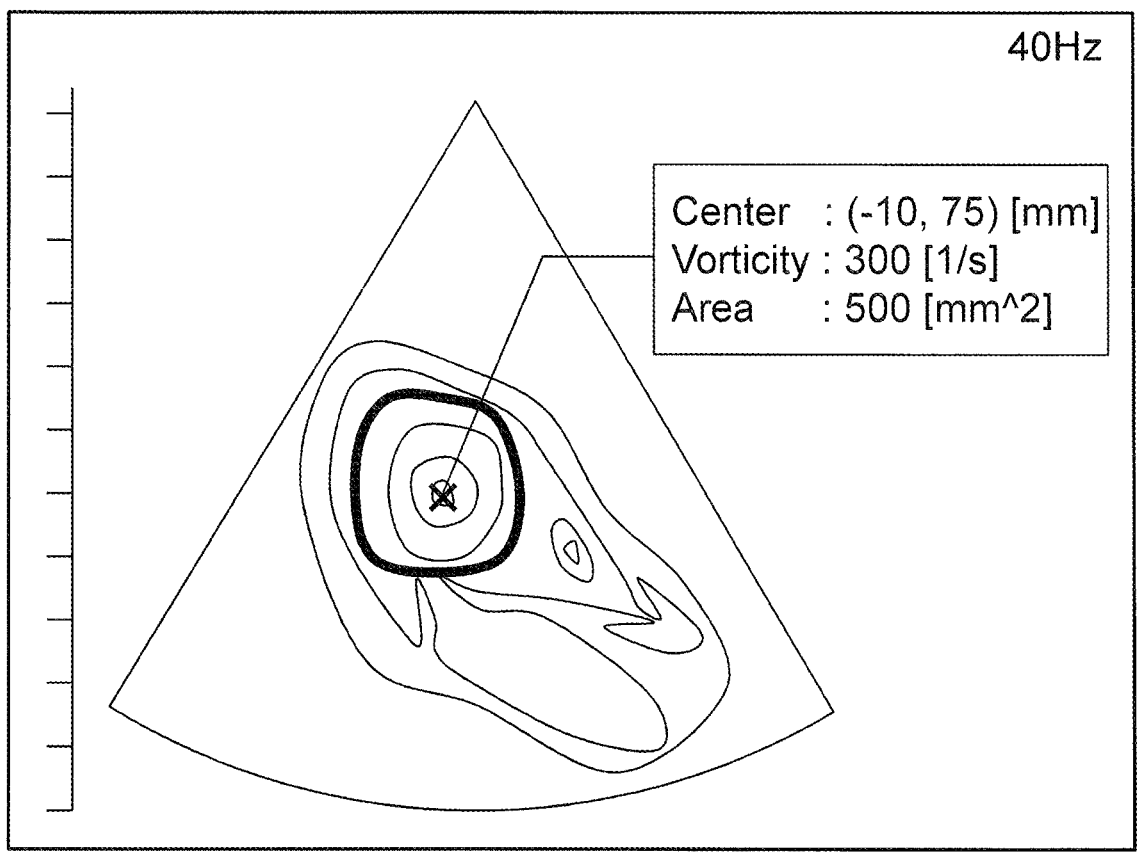

[FIG. 11]
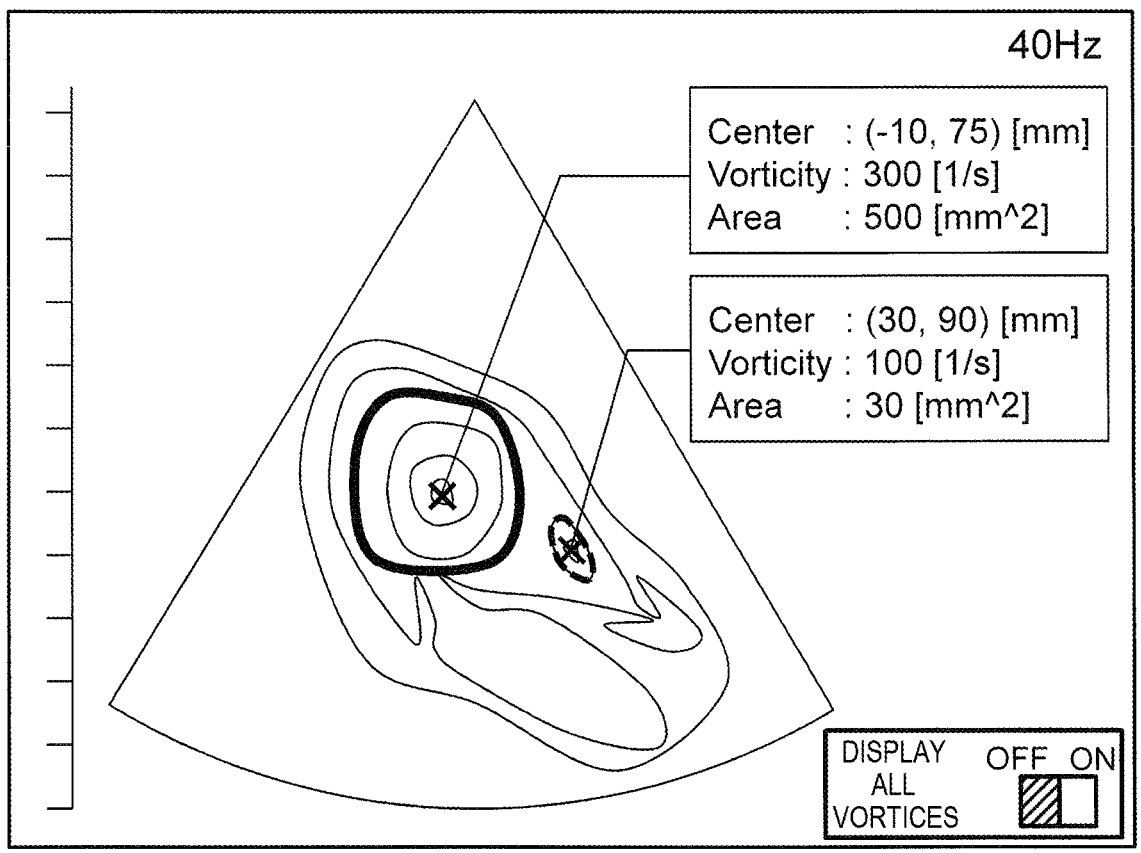

[FIG. 12]
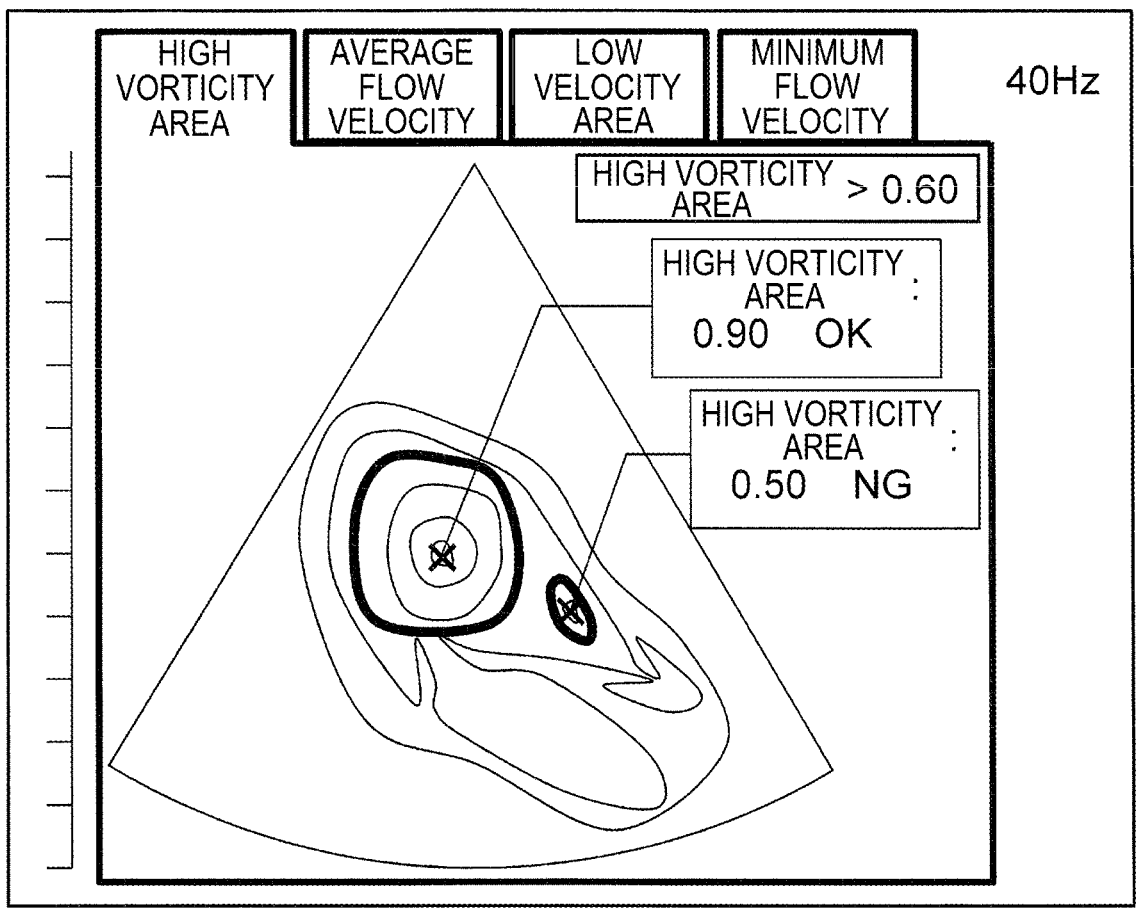

[FIG. 13]
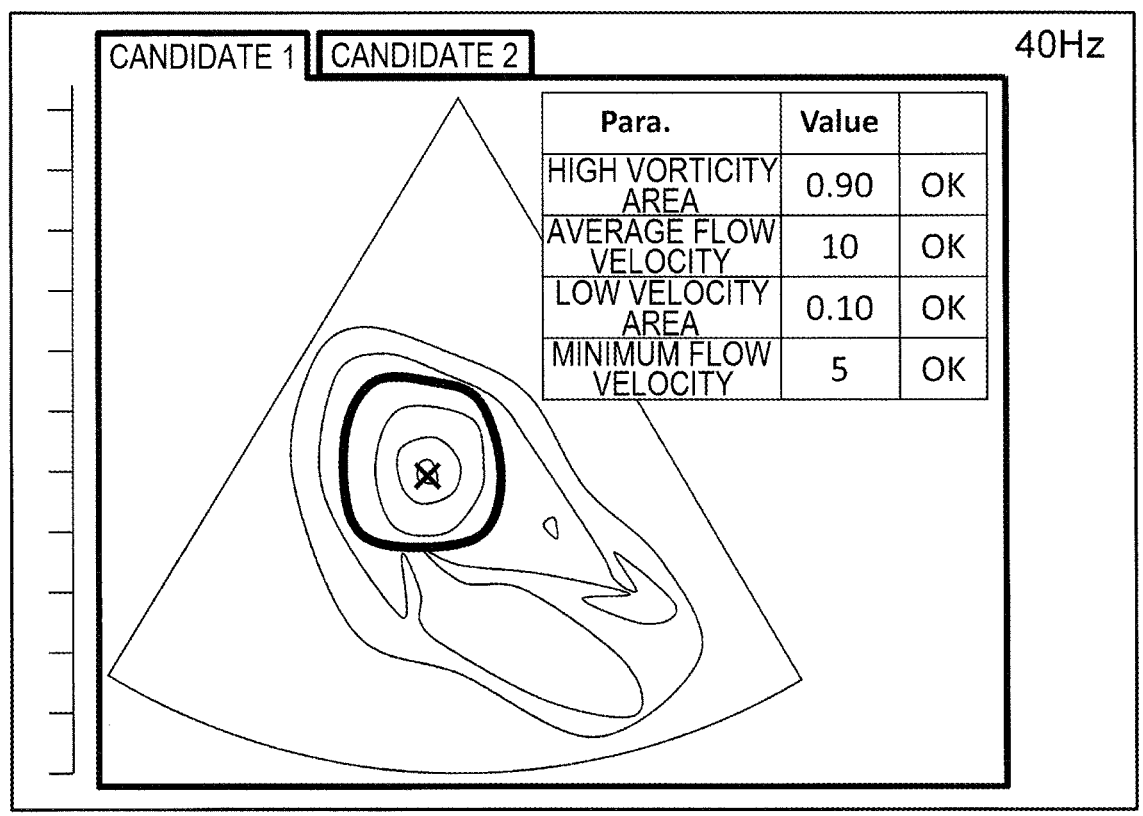

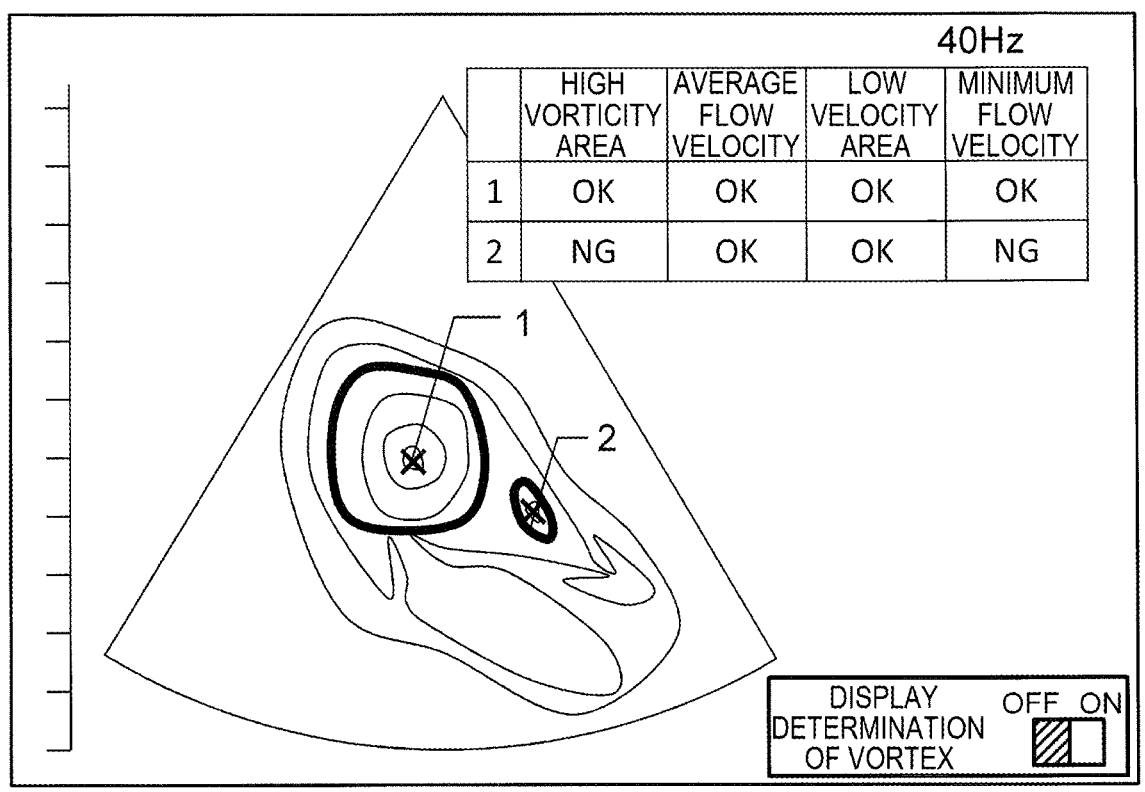
[FIG. 14]

[FIG. 15]
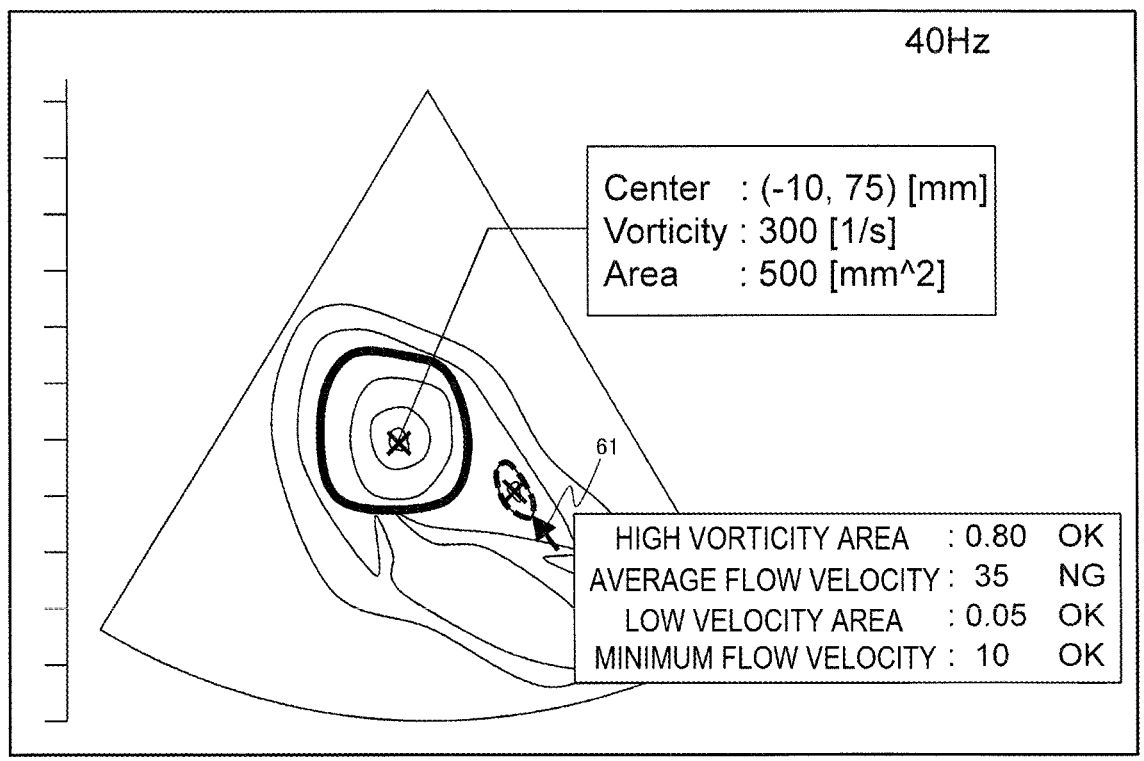

[FIG. 16]
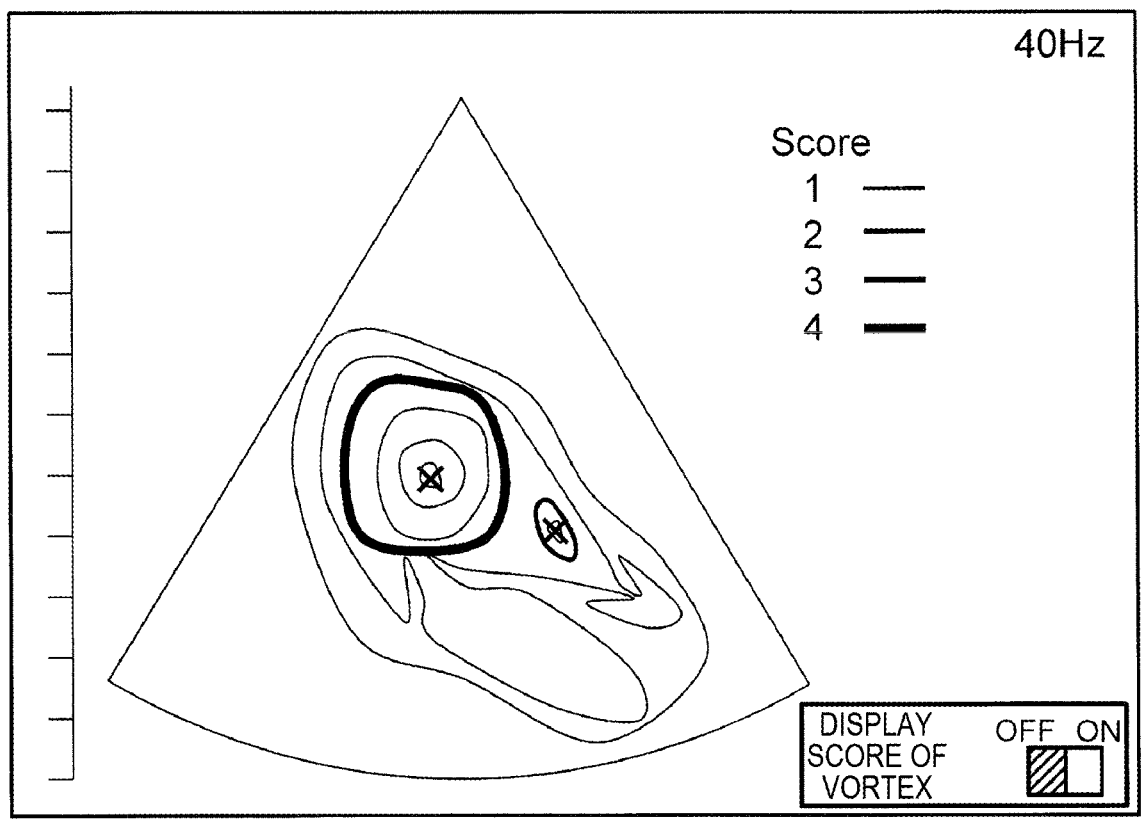

[FIG. 17]
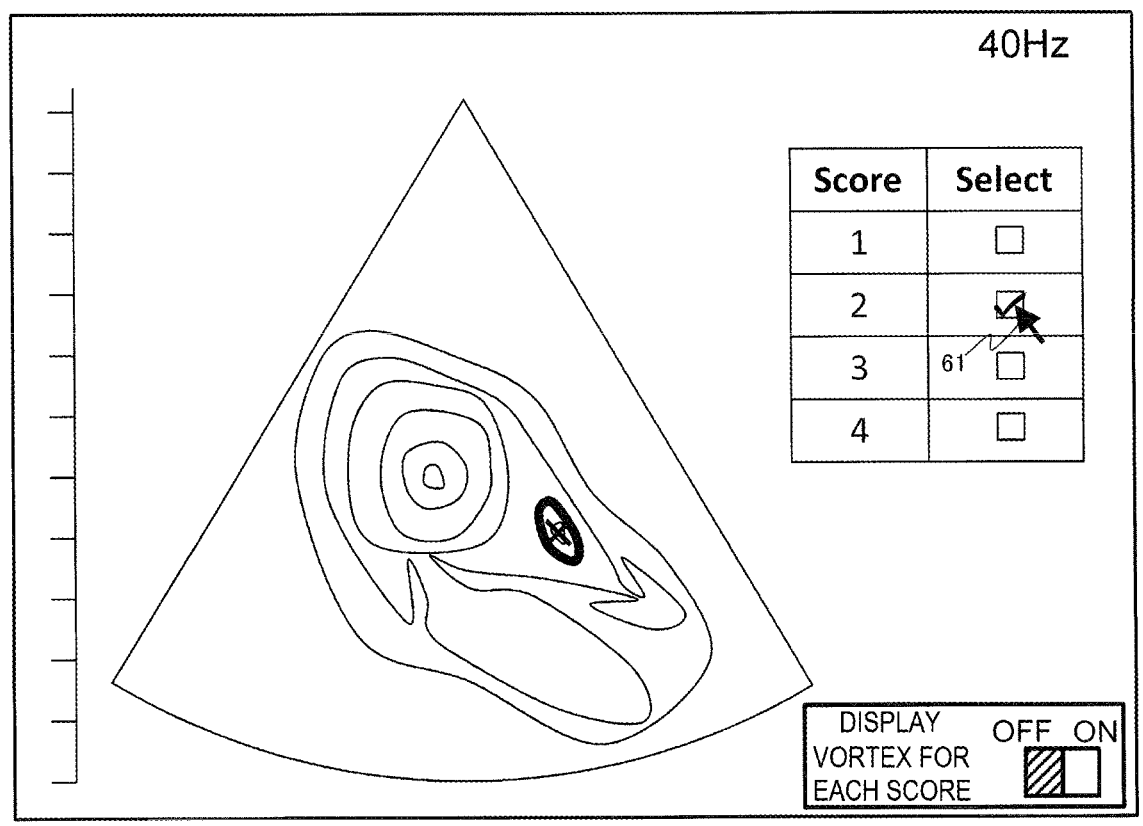

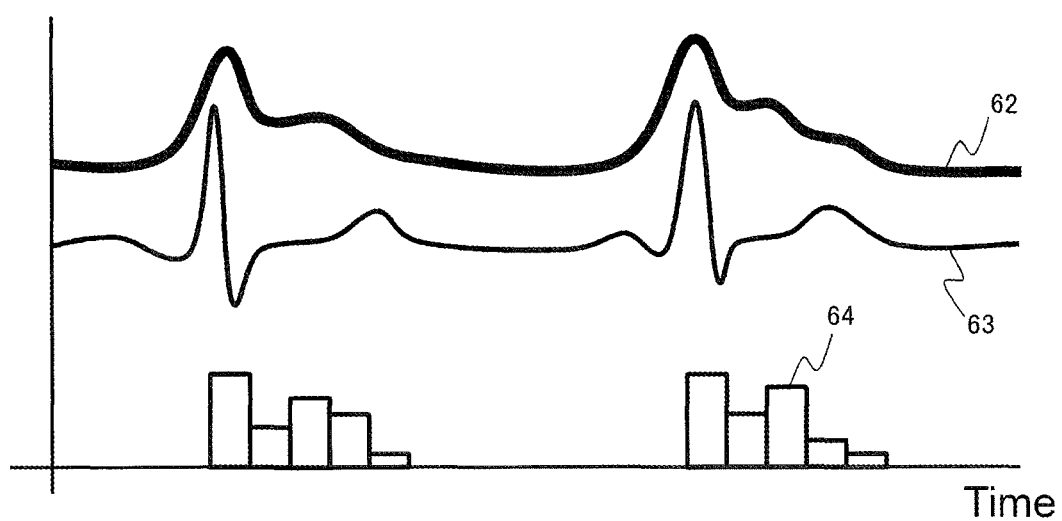
[FIG. 18]

[FIG. 19]
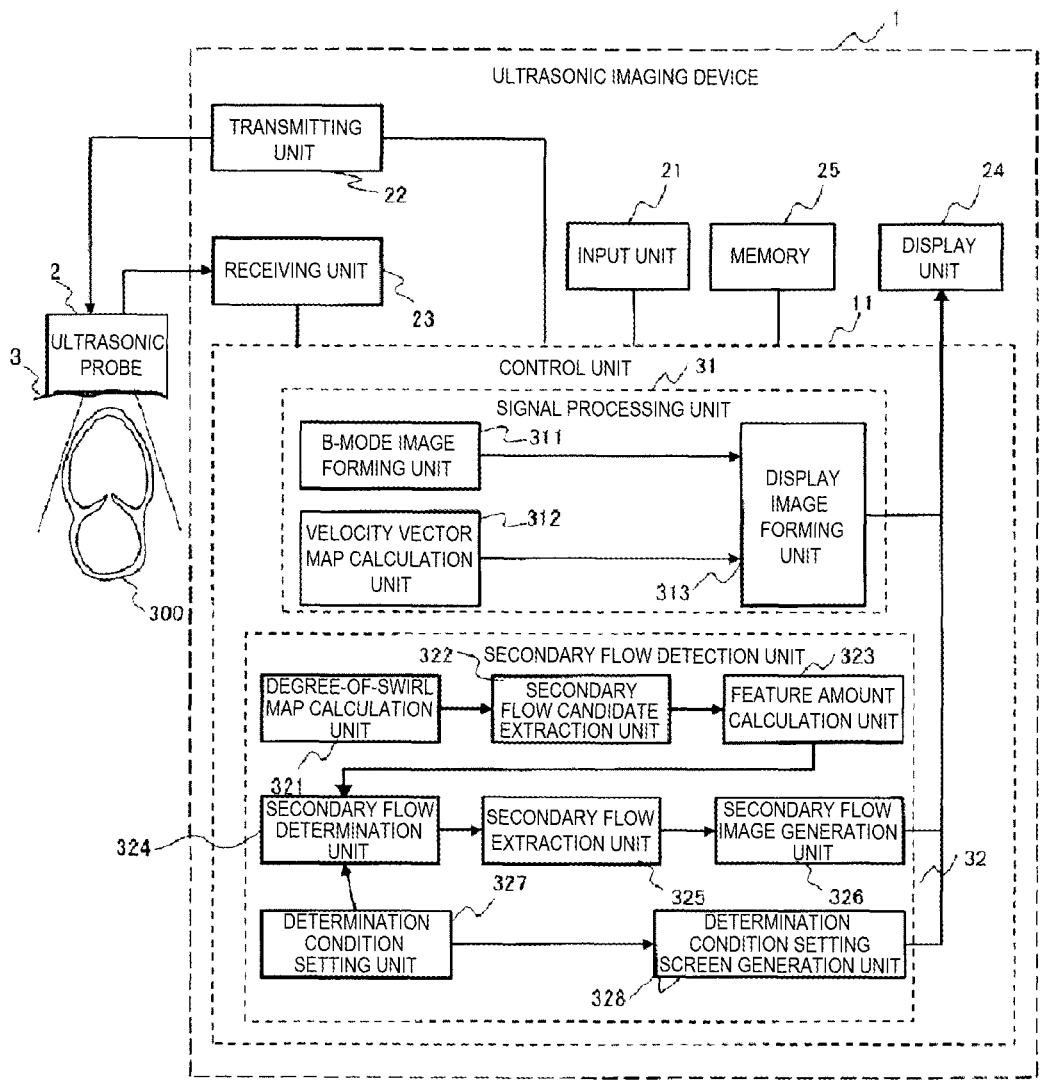

[FIG. 20]
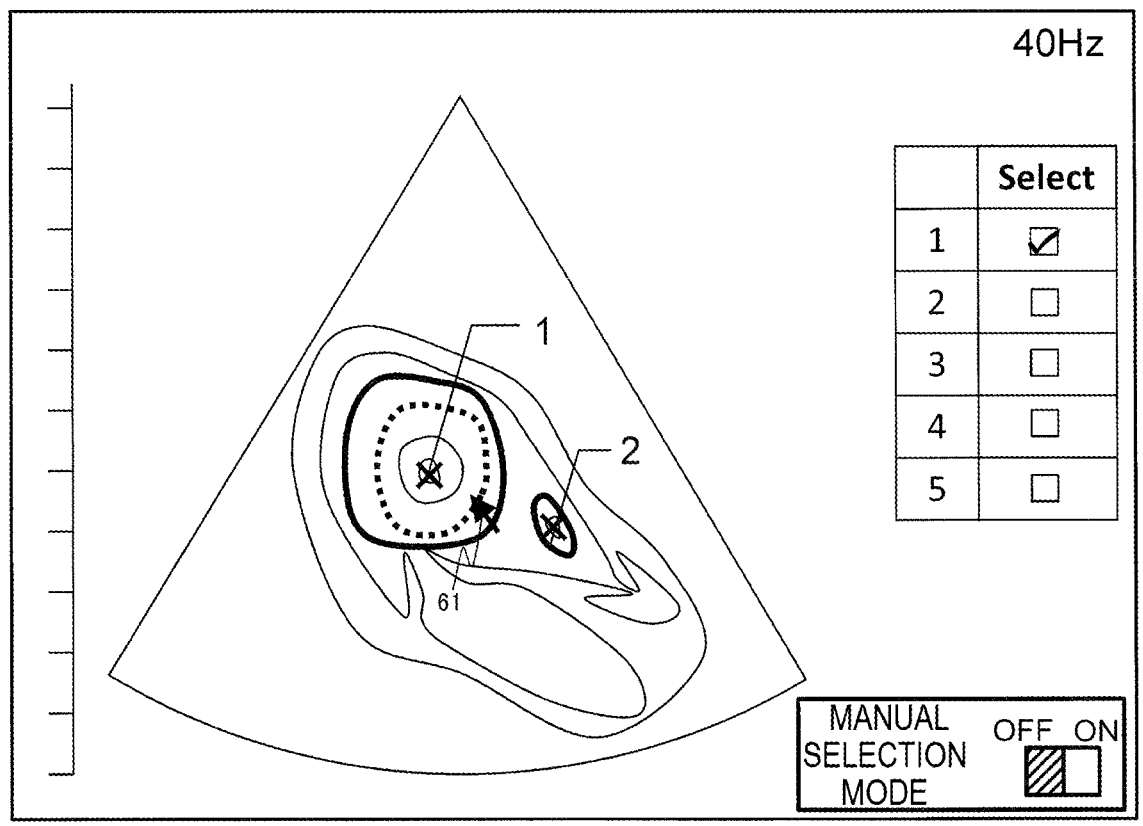

SECONDARY FLOW DETECTION DEVICE, SECONDARY FLOW DETECTION PROGRAM, AND ULTRASONIC SIGNAL PROCESSING DEVICE

TECHNICAL FIELD

The present invention relates to a secondary flow detection device, a secondary flow detection program, and an ultrasonic signal processing device, particularly to a secondary flow detection device, a secondary flow detection program, and an ultrasonic signal processing device that detect a secondary flow such as a vortex or a spiral flow in blood flow velocity measurement.

BACKGROUND ART

In an ultrasonic imaging device, there is known a technique for obtaining diagnosis information related to a blood flow, such as blood flow velocity measurement, based on a received signal obtained by transmitting and receiving ultrasonic waves to and from a subject.

In recent years, cardiovascular disease has been exemplified as one of the leading causes of death in developed countries, and it has been pointed out that abnormal cardiovascular blood vessels exhibit different blood flows from healthy cardiovascular blood vessels. Therefore, evaluating the difference in blood flow between the abnormal cardiovascular blood vessels and the healthy cardiovascular blood vessels is useful in determining the severity of cardiovascular disease and in determining treatment of cardiovascular disease.

For example, the blood flow in the left ventricle of the heart is known to produce a vortex with pulsation. It has been pointed out that in the case of a heart failure patient, the strength and magnitude of the vortex and the time for the vortex to disappear may be different from those of a healthy person. In addition, there are also research examples that suggest a relationship between a spiral flow generated in an aortic arch and aortic dissection. Therefore, a technique for detecting a secondary flow such as a vortex or a spiral flow is needed in the blood flow velocity measurement using the above-mentioned ultrasonic imaging device.

In blood flow measurement in the ultrasonic imaging device, two-dimensional or three-dimensional velocity vectors at every coordinates, that is, a velocity vector map can be obtained by using methods such as, in particular, a vector Doppler method, a speckle tracking method, and a vector flow mapping method. A user such as a doctor determines the presence or absence of the secondary flow by looking at these velocity vector maps and streamlines calculated based on the above.

However, differences occur among a plurality of users in determining, for example, a state where it is difficult to determine whether the flow travels one cycle although the flow swirls halfway, or a state where the vortex breaks down over time in the velocity vector map. In observation of a three-dimensional flow, since three-dimensional space grasp is required, it is difficult to perform determination, and differences in determination among users easily occur. Therefore, a method that can uniformly determine the presence or absence and a magnitude of the secondary flow is needed.

Therefore, for example, PTL 1 proposes an ultrasonic diagnostic device that detects a secondary flow based on a two-dimensional velocity vector map. In the ultrasonic diagnostic device in PTL 1, it is focused on that velocity vectors are arranged in a ring shape in the vortex, and the vortex in a fluid is detected based on a fact whether the flow (streamline) of the fluid obtained by tracking the velocity vector satisfies a regression condition. That is, the vortex is determined by providing a threshold value for a distance between a starting point of the streamline and points on the streamline obtained sequentially.

As another general method for detecting the secondary flow based on the velocity vector map, there is a method using a spatial velocity gradient between the velocity vectors. For example, a vorticity calculated based on the velocity gradient indicates the strength of the flow swirl. However, even when there is a difference in the strength in most of the blood flow, a swirl component is included, and the vorticity is rarely zero. Therefore, detecting the vortex by providing the threshold value for the vorticity can be considered.

PRIOR ART LITERATURE

Patent Literature

PTL 1: JP-A-2015-188736

SUMMARY OF INVENTION

Technical Problem

However, the vortex (secondary flow) determination in the ultrasonic diagnostic device in PTL 1 determines the vortex based on the regression condition of the streamline that is a feature of a spatial arrangement of the velocity vectors in a large range (macroscopic feature of the velocity vector map), and this alone may cause miss and false detection of the secondary flow.

For example, in actual measurement, the velocity vector map has a certain spatial resolution, and the streamline is drawn by connecting measurement points of the velocity vector. However, when the spatial resolution is low, there is no measurement point of the velocity vector near a location where a regressed streamline and the starting point are closest to each other, so that the regression condition is not satisfied and the secondary flow cannot be detected, that is, miss detection of the secondary flow may occur. On the contrary, in a region where the flow stagnates, adjacent measurement points are connected in a ring shape by the arrangement of the velocity vectors generated as a variation in measurement, and may be falsely detected as the secondary flow. When such a situation occurs, it is difficult to accurately check the presence or absence and duration of the vortex.

The same problem also occurs in the determination based on the vorticity obtained based on the velocity gradient between the adjacent velocity vectors (microscopic feature of the velocity vector map). Since the vorticity is a parameter defined by the velocity gradient, the value tends to increase as the velocity increases. Therefore, the vorticity is calculated to be larger for a flow that makes a U-turn at a higher velocity than a flow that swirls at a low velocity. As a result, the flow that makes the U-turn at the higher velocity is detected as the secondary flow while the flow that swirls at the low velocity is not detected as the secondary flow, that is, miss or false detection occurs.

These problems lie in the complexity of what human beings call the vortex and the spiral flow. Human beings perform comprehensive determination based on both the macroscopic feature and the microscopic feature of the above-mentioned velocity vector map to make a determination of finding the secondary flow in particular called the vortex or the spiral flow. Therefore, in the determination based on only one of the macroscopic feature and the microscopic feature, a divergence occurs with the determination made by human beings.

The invention has been made in view of the above circumstances, and an object of the invention is to uniformly extract a secondary flow based on quantitative calculation even in a complicated blood flow in a heart chamber or a blood vessel.

Solution to Problem

In order to solve the above problem, the invention provides the following means.

One aspect of the invention provides a secondary flow detection device including: a degree-of-swirl map calculation unit that obtains a velocity vector map calculated based on an echo signal reflected by an inspection target, calculates, as a value indicating a degree of a spatial change of a velocity vector, a degree of swirl based on the velocity vector map, and calculates, as a degree-of-swirl map, a spatial distribution of an iso-degree-of-swirl line obtained by connecting the degree of swirl of an equal value; a secondary flow candidate extraction unit that extracts, as a secondary flow candidate, an iso-degree-of-swirl line satisfying a predetermined condition among the iso-degree-of-swirl line indicated in the degree-of-swirl map; a feature amount calculation unit that calculates a feature amount of the velocity vector inside the secondary flow candidate; a secondary flow determination unit that determines whether the secondary flow candidate is a desired secondary flow based on the feature amount; and a secondary flow extraction unit that extracts and outputs the secondary flow determined by the secondary flow determination unit.

Another aspect of the invention provides a secondary flow detection program causing a computer to execute: a degree-of-swirl map calculation step of obtaining a velocity vector map calculated based on an echo signal reflected by an inspection target, calculating, as a value indicating a degree of a spatial change of a velocity vector, a degree of swirl based on the velocity vector map, and calculating, as a degree-of-swirl map, a spatial distribution of an iso-degree-of-swirl line obtained by connecting the degree of swirl of an equal value; a secondary flow candidate extraction step of extracting, as a secondary flow candidate, an iso-degree-of-swirl line satisfying a predetermined condition among the iso-degree-of-swirl line indicated in the degree-of-swirl map; a feature amount calculation step of calculating a feature amount of the velocity vector inside the secondary flow candidate; a secondary flow determination step of determining whether the secondary flow candidate is a desired secondary flow based on the feature amount; and a secondary flow extraction step of extracting and outputting the secondary flow determined by a secondary flow determination unit.

Yet another aspect of the invention provides an ultrasonic signal processing device including the secondary flow detection device.

Advantageous Effect

According to the invention, the secondary flow can be uniformly extracted based on quantitative calculation even in a complicated blood flow in a heart chamber or a blood vessel.

BRIEF DESCRIPTION OF DRAWINGS

FIG. 1 is a block diagram showing a schematic configuration of an ultrasonic imaging device to which a secondary flow detection device according to an embodiment of the invention is applied.

FIG. 2 is a reference diagram showing an example of a velocity vector map.

FIG. 3 is a reference diagram showing an example of a degree-of-swirl map.

FIG. 4 is a reference diagram showing an example of a display screen with a secondary flow candidate extracted.

FIG. 5 is a reference diagram showing an example of a display screen with a secondary flow candidate extracted.

FIG. 6 is a flowchart showing a flow of a secondary flow detection processing in the ultrasonic imaging device to which the secondary flow detection device according to the embodiment of the invention is applied.

FIGS. 7A and 7B are graphs in which feature amounts are plotted in view of a relationship between an average flow velocity and a high vorticity area in order to determine a secondary flow.

FIG. 8A is a linear function, and FIG. 8B shows a sigmoid function.

FIG. 9 is a table showing a relationship between a secondary flow candidate and a determination condition.

FIG. 10 is a reference diagram showing an example of a display screen generated using a secondary flow and other images.

FIG. 11 is a reference diagram showing an example of a display screen generated using a secondary flow and other images.

FIG. 12 is a reference diagram showing an example of a display screen generated using a secondary flow and other images.

FIG. 13 is a reference diagram showing an example of a display screen generated using a secondary flow and other images.

FIG. 14 is a reference diagram showing an example of a display screen generated using a secondary flow and other images.

FIG. 15 is a reference diagram showing an example of a display screen generated using a secondary flow and other images.

FIG. 16 is a reference diagram showing an example of a display screen generated using a secondary flow and other images.

FIG. 17 is a reference diagram showing an example of a display screen generated using a secondary flow and other images.

FIG. 18 is a reference diagram when a part or all of values of feature amounts used for determining a secondary flow or other quantitative values not used for determining the secondary flow, such as the number of the secondary flow for each frame are presented to a user.

FIG. 19 is a block diagram showing a schematic configuration of an ultrasonic imaging device to which a secondary flow detection device according to a modification of the embodiment of the invention is applied.

FIG. 20 is a reference diagram showing a determination condition setting screen presented when a user inputs a determination condition of a secondary flow.

DESCRIPTION OF EMBODIMENTS

Figure 8A:
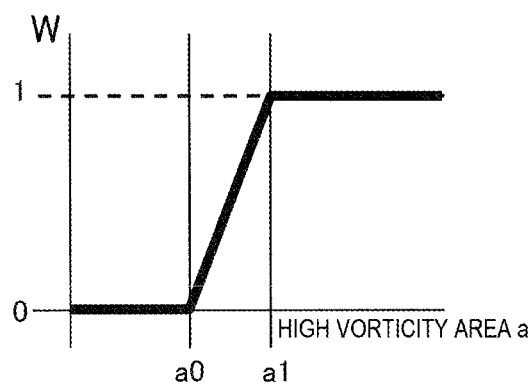
FIGS. 8A and 8B show functions for determining a secondary flow.

A secondary flow detection device according to an embodiment of the invention performs a processing on an echo signal obtained by an ultrasonic imaging device. By applying the secondary flow detection device to the ultrasonic imaging device, a secondary flow such as a vortex can be detected in an ultrasonic image captured by the ultrasonic imaging device. In the following description, an example in which the secondary flow detection device is applied to the ultrasonic imaging device will be described.

Hereinafter, the ultrasonic imaging device to which the secondary flow detection device according to the embodiment of the invention is applied will be described in more detail with reference to the drawings.

As shown in FIG. 1, the ultrasonic imaging device generates an ultrasonic image while controlling an ultrasonic probe 2 that is connected to a device main body 1.

The ultrasonic probe 2 is in contact with a living body 3 of a user, irradiates a cardiovascular blood vessel 300 in the living body 3 with ultrasound according to a signal generated in the device main body 1, receives the ultrasound reflected from the living body 3 and outputs the ultrasound to a receiving unit 23. The ultrasonic probe 2 generates a continuous wave or a pulse wave according to a scanning method, and captures a two-dimensional cross-sectional image or a three-dimensional stereoscopic image.

The device main body 1 includes an input unit 21 that inputs imaging conditions and the like to the ultrasonic imaging device, a transmitting unit 22, the receiving unit 23, a display unit 24, a memory 25, and a control unit 11 that controls the entire ultrasonic imaging device 1.

The input unit 21 includes a keyboard or a pointing device (not shown) for a doctor or a technician (hereinafter collectively referred to as a user) who operates the ultrasonic imaging device to set operating conditions of the ultrasonic imaging device for the control unit 11, and receives an input instruction from the pointing device by the user. In addition, when information from an external device such as an electrocardiogram is used in the ultrasonic imaging device, input of the information from the external device is received.

The transmitting unit 22 includes an oscillator for generating a signal of a predetermined frequency, and transmits a drive signal to the ultrasonic probe 2. The receiving unit 23 includes a receiving circuit and an analog-to-digital (A/D) converter whose sampling frequency is usually 10 MHz to 50 MHz. In addition, the receiving unit performs signal processing such as phasing addition, detection, and amplification on the echo signal received from the ultrasonic probe 2.

The A/D converter may be provided in front of a signal processing unit 31 described later instead of the receiving unit 23, and in this case, the signal processing unit 31 performs the signal processing such as phasing addition, detection, and amplification. The receiving unit 23 may include a received data memory (not shown) that temporarily stores an echo signal for each receiving element of the ultrasonic probe 2 or for each opening portion in which elements are bundled.

The display unit 24 displays various images including the ultrasonic image generated in the control unit 11 described later. The memory 25 temporarily stores the echo signal, information (information and the like instructed by the user using the input unit 10) necessary for various calculations in the control unit 11 and calculation results (a B-mode image, a display image of a velocity vector map and the like).

The control unit 11 controls the entire ultrasonic imaging device 1, and implements functions of the signal processing unit 31 that performs a predetermined processing on the echo signal obtained by the receiving unit 23 to generate an image and a secondary flow detection unit 32 that detects the secondary flow based on a velocity map generated by the signal processing unit 31.

The functions of the above-mentioned units implemented by the control unit 11 can be implemented as software by causing the control unit 11 to read and execute a program stored in advance in the memory such as a magnetic disk (not shown). A part or all of operations executed by respective units included in the control unit 11 can be implemented by an application specific integrated circuit (ASIC) or a field-programmable gate array (FPGA).

The signal processing unit 31 calculates various types of information useful for diagnosis of the velocity vector map based on the echo signal obtained by the receiving unit 23. Therefore, the signal processing unit 31 includes a B-mode image forming unit 311 that calculates the ultrasonic image such as a tomographic image called a B-mode image and other various processing data used for the ultrasonic diagnosis, a velocity vector map calculation unit 312 that generates the velocity vector map, and a display image forming unit 313 that generates a display image for displaying generated image data.

The velocity vector map calculation unit 312 may calculate the velocity vector map by any method that can obtain a spatial distribution of the velocity vector, such as a vector Doppler method, a speckle tracking method, and a vector flow mapping method. The generated velocity vector map can be displayed on the display unit 24. An example of the velocity vector map is shown in FIG. 2. FIG. 2 shows a spatial distribution of a velocity vector 301 in a left ventricle 300.

The secondary flow detection unit 32 receives the velocity vector map from the signal processing unit 31 and detects the secondary flow based on the velocity vector map. Therefore, the secondary flow detection unit 32 includes a degree-of-swirl map calculation unit 321, a secondary flow candidate extraction unit 322, a feature amount calculation unit 323, a secondary flow determination unit 324, a secondary flow extraction unit 325, and a secondary flow image generation unit 326.

The degree-of-swirl map calculation unit 321 obtains the velocity vector map calculated based on the echo signal reflected by a subject that is an inspection target, calculates a degree of swirl as a value indicating a degree of a spatial change of the velocity vector based on the velocity vector map, and calculates a degree-of-swirl map as a spatial distribution of iso-degree-of-swirl lines obtained by connecting the degree of swirl indicating equal values. An example of the degree-of-swirl map is shown in FIG. 3. FIG. 3 shows four iso-degree-of-swirl lines 302 in the left ventricle 300.

More specifically, the degree-of-swirl map calculation unit 321 obtains the velocity vector map output by the signal processing unit 31, calculates the degree of swirl at each measurement point based on a velocity gradient between adjacent velocity vectors based on the velocity vector map, and calculates the degree-of-swirl map that is the spatial distribution thereof. Note that an index calculated based on the velocity gradient of the velocity vector map and indicating the strength of swirl is collectively referred to as a degree of swirl. The representative degree of swirl is the vorticity which is a hydrodynamic parameter. The strength of swirl, for example, may be simply defined based on the absolute value of the velocity gradient, or the strength of swirl may be defined based on the product of respective direction components of the velocity gradient.

Since the degree of swirl is a microscopic feature of the velocity vector map, it is desirable to obtain the velocity gradient in a narrow range. However, the degree of swirl may be obtained after applying a decimation processing to the velocity vector map. The degree of swirl also may be calculated after applying an arithmetic processing such as a spatial smoothing processing, a temporal smoothing processing between frames, and a mask processing excluding a range of interest.

After calculating the degree-of-swirl map, an arithmetic processing such as a spatial smoothing processing or a temporal smoothing processing between frames, a mask processing excluding a range of interest may be applied to the degree-of-swirl map. Particularly, the smoothing processing on the velocity vector map or the degree-of-swirl map has an effect of preventing an abnormally large degree of swirl from being calculated in calculation of the degree of swirl including differential calculation in which a calculated value is likely to be unstable.

The secondary flow candidate extraction unit 322 extracts, as a secondary flow candidate, an iso-degree-of-swirl line satisfying a predetermined condition among iso-degree-of-swirl lines indicated in the degree-of-swirl map calculated by the degree-of-swirl map calculation unit 321. That is, the secondary flow candidate extraction unit 322 extracts, as the secondary flow candidate, an iso-degree-of-swirl line having a degree of swirl satisfying the predetermined condition from the degree-of-swirl map, and determines, as a representative point of the secondary flow candidate, a point where the degree of swirl satisfies the determined condition.

A representative condition for determining the secondary flow candidate is an iso-degree-of-swirl line having a degree of swirl exceeding a predetermined threshold value. A representative condition for selecting the representative point of the secondary flow candidate is a point where the degree of swirl takes an extreme value. Examples of a display screen with a secondary flow candidate extracted are shown in FIG. 4 and FIG. 5. FIG. 4 and FIG. 5 show an extracted secondary flow candidate 330, a point where the degree of swirl is maximum, and a range where the velocity is zero.

As an effect of extracting the secondary flow candidate based on the degree of swirl, there is an effect of eliminating the miss detection of the secondary flow candidate. This is because the point where the degree of swirl takes the extreme value is necessarily included within the range as a minimum necessary condition for a desired secondary flow. When the secondary flow candidate is searched based on a macroscopic feature of a spatial arrangement of the velocity vector, it is difficult to extract the secondary flow candidate without any omission or without being affected by conditions such as the threshold value. The condition for determining the representative point of the secondary flow candidate or the secondary flow candidate range may be a predetermined fixed condition, or may be given by the user using the input unit 10.

In addition, the condition may be automatically determined every time a secondary flow detection processing is performed. When the condition is automatically determined, the condition may be determined based on a maximum velocity or an average velocity of the velocity vector map in a target frame, or may be determined based on a maximum degree of swirl or an average degree of swirl of the degree-of-swirl map.

Furthermore, the condition may be determined based on other information, for example, information from an external device such as an electrocardiogram. The condition for determining the secondary flow candidate range may be determined in association with the representative point of the secondary flow candidate. For example, the threshold value of the degree of swirl that determines the secondary flow candidate range may be determined based on the degree of swirl of the representative point of the secondary flow candidate.

The feature amount calculation unit 323 calculates at least the feature amount of the velocity vector inside the iso-degree-of-swirl line that is the secondary flow candidate, and calculates the feature amount of the velocity vector outside the iso-degree-of-swirl line that is the secondary flow candidate and near the iso-degree-of-swirl line if necessary. More specifically, the feature amount calculation unit 323, regarding the secondary flow candidate extracted by the secondary flow candidate extraction unit 322, calculates the feature amount of the velocity vector based on the feature indicating the spatial arrangement of the velocity vectors (macroscopic feature) within and outside the secondary flow candidate range (inside and outside the iso-degree-of-swirl line). At this time, the feature amount may be calculated based on velocity information, or may be obtained by, for example, converting the velocity vector map into another form such as a streamline.

Although the number of the feature amount calculated may be one, it is desirable to calculate a plurality of feature amounts in order to realize secondary flow detection reflecting the complexity of human beings in determining the secondary flow. The feature amount calculated by the feature amount calculation unit 323 includes at least a feature amount based on the macroscopic feature of the velocity vector, and in addition, may include, for example, a feature amount based on a shape of the secondary flow candidate range, a coordinate of the representative point of the secondary flow candidate, or the velocity gradient.

The secondary flow determination unit 324 determines whether the secondary flow candidate is the desired secondary flow based on the feature amount calculated by the feature amount calculation unit 323. Herein, the desired secondary flow is a secondary flow that the user focuses on as a diagnosis determination material. As a determination method thereof, there are a plurality of methods described later, and one of the methods may be performed, or two or more may be performed to present a plurality of results to the user.

The secondary flow extraction unit 325 extracts and outputs the secondary flow determined by the secondary flow determination unit 324. The secondary flow image generation unit 326 draws the secondary flow extracted by the secondary flow extraction unit 325 and generates image data to be displayed on the display unit 14.

A case where the secondary flow is detected in the ultrasonic imaging device configured in this way will be described with reference to a flowchart of FIG. 6. In the following description, an example in which the secondary flow detection unit 32 extracts the vortex as a two-dimensional secondary flow based on a two-dimensional velocity vector map will be described.

The degree-of-swirl map calculation unit 321 obtains the velocity vector map (see FIG. 2) from the signal processing unit 31 in step S1, and calculates a degree of swirl at each measurement point based on the velocity gradient between adjacent velocity vectors in the velocity vector map to calculate a spatial distribution as the degree-of-swirl map in step S2. The spatial distribution of the degree of swirl can be drawn using, for example, the iso-degree-of-swirl line obtained by connecting the equal degree of swirl (see FIG. 3).

In the present embodiment, the vortex is used as the secondary flow, so the vorticity is used here as the degree-of-swirl. A definition formula of the hydrodynamic vorticity is shown in the following formula (1).

$$\Omega = rot\vec{v} = \left(\frac{\partial v_z}{\partial y} - \frac{\partial v_y}{\partial z}, \frac{\partial v_x}{\partial z} - \frac{\partial v_z}{\partial x}, \frac{\partial v_y}{\partial x} - \frac{\partial v_x}{\partial y}\right) \quad (1)$$

Here, $\Omega$ represents the vorticity, v with an arrow represents the velocity vector, and x, y, and z represent coordinate axes. When the velocity vector is two-dimensional, the formula for obtaining the vorticity is simplified as the following formula (2).

$$\Omega = \frac{\partial v_y}{\partial x} - \frac{\partial v_x}{\partial y} \quad (2)$$

According to the above formula (1), the vorticity is a three-component vector when the velocity vector is three-dimensional, and according to formula (2), the vorticity is a one-component value when the velocity vector is two-dimensional. The positive or negative sign of each component represents the direction of rotation, and a large absolute value of each component indicates a strong rotation of the flow in that direction.

The degree-of-swirl map output by the degree-of-swirl map calculation unit 321 may be a distribution of values having positive and negative information or may be a distribution of absolute values when the velocity vector is two-dimensional. When the velocity vector is three-dimensional, three distributions for each component may be calculated respectively, or the degree-of-swirl map may be a distribution of absolute values.

In an actual velocity vector map, adjacent velocity vectors may have significantly different values or may be directed in significantly different directions due to measurement variations. In that case, the degree of swirl is calculated as an abnormally large value. In order to avoid this situation, it is effective to apply spatial or temporal smoothing to the velocity vector map.

Alternatively, spatial or temporal smoothing may be applied to the calculated degree-of-swirl map. Alternatively, as another problem, an abnormally large degree of swirl may be calculated because the velocity is discontinuous near a wall. In order to avoid such a problem, it is effective to perform a processing of applying a mask to a region where the degree of swirl is not calculated, or applying a weight to converge the velocity near the wall to zero.

Next, in step S3, the iso-degree-of-swirl line satisfying the predetermined condition is extracted as the secondary flow candidate by the secondary flow candidate extraction unit 322. After the degree-of-swirl map calculated by the degree-of-swirl map calculation unit 321 is received, the iso-degree-of-swirl line having the degree of swirl satisfying the predetermined condition is extracted as the secondary flow candidate, and the point where the degree of swirl satisfies the determined condition is determined as the representative point of the secondary flow candidate.

The representative condition for determining the representative point of the secondary flow candidate is, for example, that the degree of swirl takes the extreme value. The point where the degree of swirl takes a maximum value (minimum value according to a flow direction of the vortex) is a portion where the swirling flow is strongest in the vicinity thereof. In addition, the representative condition for determining the secondary flow candidate is the iso-degree-of-swirl line having the degree of swirl exceeding the predetermined threshold value.

The threshold value may be predetermined based on clinical data, fluid simulation, or the like, or may be a numerical value given by the user. In addition, for example, different conditions may be used for a velocity vector map having a generally high flow velocity and a velocity vector map having a stagnating flow. The conditions are determined by a method based on information, such as the velocity vector map or the degree-of-swirl map, calculated by the ultrasonic imaging device, and a determining method based on information from the external device such as the electrocardiogram.

The effect of changing the condition for determining the representative point of the secondary flow candidate or the secondary flow candidate for each velocity vector map is not to miss the secondary flow in a velocity vector map with a slow flow while avoiding excessive secondary flow candidates being detected in the a velocity vector map with a fast flow in which a strong secondary flow is likely to form. In particular, the effect of changing the condition for determining the representative point of the secondary flow candidate or the range of the secondary flow candidate based on the velocity vector, the degree of swirl, and the electrocardiogram obtained for each patient is to extract the secondary flow without missing even in a patient whose cardiopulmonary function is reduced due to cardiovascular disease or a surgery and the strong secondary flow is difficult to form.

In the next step S4, the feature amount calculation unit 323 calculates the feature amount of the velocity vector based on the secondary flow candidate and the representative point thereof extracted by the secondary flow candidate extraction unit 322 and based on the macroscopic feature of the velocity vectors within and outside the secondary flow candidate range (inside and outside the iso-degree-of-swirl line). Herein, as the feature amount of the secondary flow, in addition to a value obtained by quantifying the feature of a macroscopic spatial arrangement of the velocity vectors, a quantitative value based on, for example, the shape of the iso-degree-of-swirl line indicating the secondary flow candidate, the coordinate of the representative point of the secondary flow candidate, or the velocity gradient, may be calculated simultaneously.

The feature amount of the secondary flow to be calculated can be set by comparing the desired secondary flow and a velocity vector map for a flow to be rejected. Herein, a two-dimensional velocity vector map of a vortex formed in the left ventricle will be described as an example.

In the left ventricle, for example, when a valve opens and a high-velocity blood flow flows, a blood flow occurs in which the inflow blood flow hits a heart wall, such as an apex of the heart, or hits existing blood to make a U-turn, and a returning blood flow is involved in the high-velocity inflow blood flow, so that a "rotating flow" occurs. As a result, for example, the velocity vector map as shown in FIG. 4 is formed, and the "rotating flow" may remain without disappearing even after the inflow of the high-velocity blood flow ends.

Such a flow is a secondary flow focused on by a doctor (that is, a desired flow). At this time, at the center of the rotating flow, a point where the velocity is zero occurs due to the effect of viscosity, and the degree of swirl is maximum substantially at the same place. Meanwhile, when the inflow velocity is not fast enough to cause involvement or when the shape cannot be kept as the vortex due to deceleration, the blood flow in the left ventricle becomes an unclosed flow, that is, a U-shaped flow, for example, as shown in FIG. 5. At this time, the velocity is zero due to the effect of viscosity at an entire boundary where the flow in the opposite direction is adjacent to the above flow. Comparing these velocity vector maps, as the feature of the macroscopic flow, there is a difference that a range where the velocity is zero is a point in the desired secondary flow and is a linear shape in the U-shaped flow.

Therefore, for example, the range where the velocity is smaller than or equal to a certain value is defined as a zero velocity range, and the desired secondary flow and the U-shaped flow can be discriminated from each other when an area of the zero velocity range in the secondary flow candidate range is used as the feature amount. That is, it can be determined that the flow is not the desired secondary flow when at least the area of the zero velocity range in the iso-degree-of-swirl line of the secondary flow candidate is large. Alternatively, a distance between the coordinate of the point where the velocity is minimum and the coordinate of the point where the degree of swirl takes the extreme value may be used as the feature amount because of the fact that a place where the swirl is strongest and a place where the velocity is zero (minimum) are almost the same in the desired secondary flow, whereas a place where the velocity is minimum does not necessarily match a place where the degree of swirl is strongest in the U-shaped flow.

The feature amount is supplementarily combined with the feature of the degree-of-swirl map based on the macroscopic feature of the spatial arrangement of the velocity vector. In addition, an absolute value of the average velocity vector obtained by averaging the velocity vectors in the iso-degree-of-swirl line of the secondary flow candidate may be used as the feature amount because of the fact that there are almost the same number of velocity vectors in any direction within the iso-degree-of-swirl line in the desired secondary flow and there are many velocity vectors in a specific direction in the iso-degree-of-swirl line in the U-shaped flow.

In that case, when the absolute value of the average velocity vector has a large value, it can be determined that the flow is not the desired secondary flow. Alternatively, a deflection angle of the velocity vector in the iso-degree-of-swirl line of the secondary flow candidate may be calculated for each measurement point, and a standard deviation thereof may be used as the feature amount. In this case, the smaller the standard deviation is, the more the directions of the velocity vectors in the iso-degree-of-swirl line of the secondary flow candidate are aligned, and it can be determined that the flow is not the desired secondary flow.

In step S5, the secondary flow determination unit 324 determines whether the extracted secondary flow candidate is the desired secondary flow based on the feature amount calculated in the feature amount calculation unit 323 for each secondary flow candidate. As shown in FIGS. 7(A) and (B), the determination method is easy to understand when a region showing the desired secondary flow is defined in an n-dimensional space including n feature amounts. Hereinafter, a representative example of a method for determining the desired secondary flow based on the feature amount will be described.

A simplest determination method is to set a threshold value for each feature amount and determine whether the threshold value is exceeded. When the features are related to each other, as shown in FIG. 7(B), a function combining a plurality of feature amounts may be defined, and the function may be used as a boundary of a region indicating the desired secondary flow in the n-dimensional space.

When the boundary and the threshold value of the region of the secondary flow are strictly defined, for example, the secondary flow detected in one frame may not be detected in the next frame due to the variation in the value of each feature amount caused by the measurement error because there is a measurement error in the actual velocity vector map.

Figure 8B:
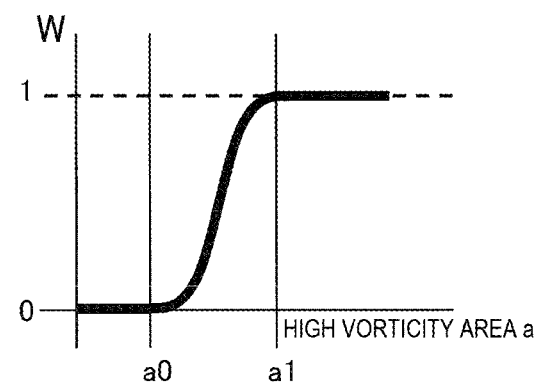

Therefore, in order to give robustness to the determination, for example, a method may be adopted in which the desired secondary flow is obtained when three or more of four threshold values are satisfied. Alternatively, a method may be adopted in which each feature amount is replaced with another value by a function W having a value between 0 and 1, such as a linear function as shown in FIG. 8(A) or a sigmoid function as shown in FIG. 8(B), and the desired secondary flow is obtained when a sum thereof exceeds a reference value. In this method, for example, a feature amount slightly smaller than the threshold value is replaced with a value such as 0.9.

An example in which the secondary flow is determined by various methods is shown in FIG. 9. Herein, there is an example in which the number of the secondary flow candidate is four and the secondary flow is determined based on the four feature amounts. First, in a method 1, determination is performed based on four conditional expressions shown in Equation (3).

$$a > 0.60, b < 30, c < 0.20, d < 20 \quad (3)$$

Herein, a represents a high vorticity area, b represents an average flow velocity, c represents a low velocity area, and d represents a minimum flow velocity.

In this case, only a candidate 1 is extracted as the desired secondary flow. Next, in a method 2, determination is performed based on three conditional expressions shown in Equation (4).

$$a > 0.60, c < 0.20, b+d < 50 \quad (4)$$

In this case, the candidate 1 and a candidate 2 are extracted as the desired secondary flow. Next, in a method 3, threshold values same as in Equation 3 are used, and when three or more of the threshold values are satisfied, it is determined that the flow is the desired secondary flow. In this case, the candidate 1, the candidate 2, and a candidate 3 are extracted as the desired secondary flow. Finally, in a method 4, each feature amount is converted to a value between 0 and 1 based on Equation 5, Equation 6, Equation 7 or Equation 8 and it is determined that the flow is the desired secondary flow when the sum of these values are 3.5 or more.

$$w = 0 (a \le a0), w = \frac{a - a0}{a1 - a0}(a0 < a < a1), w = 1(a1 \le a) \quad (5)$$

$$W = \frac{1}{1 + e^{-\alpha(a - \frac{a1-a0}{2})}} \quad (6)$$

$$w = 1(b \le b0), w = \frac{b1 - b}{b1 - b0}(b0 < b < b1), w = 0(b1 \le b) \quad (7)$$

$$W = \frac{e^{-\beta(b - \frac{b1-b0}{2})}}{1 + e^{-\beta(b - \frac{b1-b0}{2})}} \quad (8)$$

Herein, a and b represent the feature amounts, and all of the candidate 1, the candidate 2, the candidate 3, and the candidate 4 may be extracted as desired secondary flows by determining appropriate threshold values a0, a1, b0, and b1 and coefficients α and β for each feature amount.

These determination conditions may be the predetermined fixed condition, or may be given by the user using the input unit 21. In addition, the determination conditions may be automatically determined for each measurement. When the condition is automatically determined, the condition may be determined based on the maximum velocity or the average velocity of the velocity vector map in the target frame, or may be determined based on the maximum degree of swirl or the average degree of swirl of the degree-of-swirl map. Furthermore, the condition may be determined based on other information, for example, information from the external device such as the electrocardiogram.

In the following step S6, the secondary flow extraction unit 325 extracts and outputs the secondary flow determined by the secondary flow determination unit 324 to the secondary flow image generation unit 326. In the following step S7, the secondary flow image generation unit 326 draws the secondary flow extracted by the secondary flow extraction unit 325 and generates image data to be displayed on the display unit 14. That is, the secondary flow image generation unit 326 appropriately converts the extracted desired secondary flow into a display format that is easy for the user to understand. As an example of a possible display format, it is conceivable to display the representative point of the secondary flow and a boundary line of the range.

The display image forming unit 313 receives the image data generated by the secondary flow image generation unit 326, and finally, for example, a display image as shown in FIG. 10 can be formed by overlapping a morphological image such as the B-mode image and a degree-of-swirl map shown as iso-degree-of-swirl lines or color shades. At this time, a blood flow vector map or the streamline may be displayed in an overlapping manner instead of the degree-of-swirl map or in combination with the degree-of-swirl map. Further, as another display format of the secondary flow, a color may be added and displayed inside the range of the secondary flow. At this time, a gradation may be added according to the value of the degree of swirl.

Further, in the case of three-dimensional measurement, when the color is added to the display of the degree-of-swirl map or the determination result of the secondary flow, a back side thereof may not be visible, which may be inconvenient. In such a case, the strength such as the degree of swirl may be expressed using color transparency instead of color shadings, or color shadings and color transparency may be used in combination.

It is effective to show the determination process to the user in order to show the user the rationality of the determination result of the secondary flow. In addition, clarifying the determination process has an effect of identifying a reason when the determination result is different from a result desired by the user, and is helpful to manually correct the determination result or to correct the determination condition.

Therefore, the secondary flow image generation unit 326 may, in various formats, display a secondary flow candidate rejected in the determination process, display a part or all of the feature amounts of the secondary flow candidate including the rejected secondary flow candidate, or present the user a result of scoring based on the plurality of feature amounts for the secondary flow candidate including the rejected secondary flow candidate.

For example, a button or a switch having a function of displaying the secondary flow candidate including the rejected candidate is prepared in a physical or software manner, and the user operates the button or the switch to display the secondary flow candidate rejected in the determination process, as shown in FIG. 11. In FIG. 11, the boundary of the range of the secondary flow candidate finally selected is shown by a thick solid line, and the boundary of the range of the secondary flow candidate rejected in the determination process is shown by a dotted line. The button or the switch having the function of displaying the secondary flow candidate including the rejected candidate may be labeled with a function such as "display all vortices".

As shown in FIG. 12, the determination result for each determination condition may be displayed separately. In FIG. 12, tabs are provided for respective feature amounts. For example, regarding the high vorticity area that is one of the feature amounts, whether each secondary flow candidate satisfies the determination condition of 0.60 or more is displayed together with the value of the feature amount.

Alternatively, the determination result under each determination condition may be presented for each secondary flow candidate as shown in FIG. 13, and the determination result under each determination condition for each secondary flow candidate may be displayed at one time as shown in FIG. 14. In FIG. 13, the tabs are provided for secondary flow candidates 1 and 2, and for example, regarding the secondary flow candidate 1, whether each feature amount satisfies the conditional expression is displayed together with the value of the feature amount. FIG. 14 displays whether each feature amount of each secondary flow candidate satisfies the conditional expression.

In this way, as the determination process, the calculated feature amount may be displayed, or only the determination result based on the calculated feature amount may be displayed. Alternatively, as shown in FIG. 15, by locating a cursor or the like on the secondary flow candidate, the determination results under various feature amounts and determination conditions may be displayed, or the function may be combined with the various displays as described above. FIG. 15 shows a display example showing the user the determination process for the rejected secondary flow candidate by bringing a cursor 61 close to the rejected secondary flow candidate.

The coordinate, the degree of swirl, and each feature amount of the representative point for each secondary flow candidate may be separately output to the screen as a table, or may be output to the outside as an output file. As a method for scoring the secondary flow candidate based on the plurality of feature amounts, for example, the scoring may be performed by determining whether the desired secondary flow condition is satisfied under some determination conditions.

Herein, the score is a value indicating the possibility that the secondary flow candidate is the desired secondary flow. Alternatively, as shown in the determination method (4) of the secondary flow in step S5, each feature amount is appropriately converted to the value between 0 and 1, and values calculated based on these values may be used as the score. As an example of an image showing the scoring result to the user, for example, the color or the thickness of the representative point of the secondary flow or the boundary line of the range may be changed or the line type may be changed according to the score, as shown in FIG. 16.

Alternatively, when adding the color to the range of the secondary flow, the type or the shading of the color may be changed. As shown in FIG. 17, the display may be switched for each score. FIG. 17 shows an example of a display format that displays only a secondary flow candidate of a score designated by the user. A part or all of these displays may be displayed by shifting to a mode for a specific display by the user operating the button or the switch prepared in a physical or software manner.

In either display, a designated secondary flow candidate may be reclassified into the desired secondary flow by designating the representative point or the range of the secondary flow candidate rejected in the determination process. Displaying the secondary flow candidate rejected in the determination process, or reclassifying the rejected secondary flow candidate into the desired secondary flow is a function that takes advantage of the characteristic of performing detection of the secondary flow in multiple stages.

As another example of the display format, a part or all of the values of respective feature amounts used to determine the secondary flow or other quantitative values not used for secondary flow determination, such as the number of the secondary flow of each frame may be presented to the user as a chart or table arranged in time series, as shown in FIG. 18. At this time, biological information, such as an electrocardiogram signal, obtained from the external device may be displayed together. In FIG. 18, a time-series change 62 of the maximum value of the degree of swirl in the frame, an electrocardiogram 63, and a time series change 64 of the number of the secondary flow are presented to the user. Such a display has an effect of visually indicating at which time phase in the heartbeat the secondary flow is stronger or at which time phase the number of the secondary flows increases.

(Modification)

FIG. 19 is a block diagram showing a configuration example when the ultrasonic imaging device 1 includes a mechanism for the user to intuitively adjust a conditional expression for determining the secondary flow in the secondary flow determination unit 324.

Since the basic configuration is the same as that of the above-mentioned embodiment, the same reference numeral is given to the same configuration, and the description thereof is omitted. In the modification, the secondary flow determination unit 324 includes a determination condition setting unit 327 that sets a determination condition by the user and a determination condition setting screen generation unit 328 that generates a display screen for displaying the determination condition setting unit 327. The user inputs a determination condition by the input unit 21 while referring to a determination condition setting screen generated by the determination condition screen generation unit 328 and displayed on the display unit 24.

The determination condition may be set in advance before blood flow measurement or may be performed in the middle of measurement or calculation of the secondary flow detection. As an effect that the user intuitively adjusts the conditional expression for determining the secondary flow, it is possible to adjust a determination criterion of the secondary flow for the user to perform determination that is different for respective users according to respective users. Further, there is an effect of further increasing the determination accuracy by collecting determination examples from a plurality of doctors and determining the predetermined fixed condition as described in the above-mentioned embodiment based on the results.

As described above, even in a method for automatically determining the determination condition for each measurement, an effect of increasing the determination accuracy can be expected by determining the conditional expression and the parameter thereof based on the collected determination examples.

When the user determines the conditional expression for determining the secondary flow, it can be operated in the following procedure, for example.

The determination condition setting screen generation unit 328 forms an image of the representative blood flow vector map, the degree-of-swirl map, the streamline, or the like, and presents the image to the user by displaying the image on the display unit 24. The image displayed by the determination condition setting screen generation unit 328 may be an image based on an actual measurement result or an image prepared in advance.

The representative point of the secondary flow candidate and the range thereof may be shown to the user based on the calculation result of the secondary flow candidate extraction unit 322 or the calculation result prepared in advance. The user refers to the image displayed on the display unit 24, and determines whether the secondary flow is included in the image, where is the secondary flow when the secondary flow is included, or which range is considered as the secondary flow. At this time, particularly in the case of a three-dimensional image, the image may be rotated based on an input from, for example, the input unit 21 such that the user can see the image at an easy-to-view angle. In addition, any cross-sectional image may be displayed.

The user inputs the determination result using the input unit 21. For example, as shown in FIG. 20, as an input method, use may be made of a format for making a selection from a list of secondary flow candidates generated by the determination condition setting screen generation unit 327 and displayed on the display unit 24. At this time, the list of secondary flow candidates may be shown in an order based on the scoring as shown in the above-mentioned embodiment. At this time, not all the secondary flow candidates are shown, but only the secondary flow candidate with a high score may be shown.

As another input method, a format for the user to move and designate a cursor and for the input unit 21 to recognize may be used, or a format for the user to directly draw the image and for the input unit 21 to recognize may be used. For the range of the secondary flow candidate (iso-degree-of-swirl line), use may be made of a format for displaying the corresponding iso-degree-of-swirl line each time the user changes the value of the degree of swirl, and selecting the iso-degree-of-swirl line that is determined to be the outer periphery of the secondary flow, and use may be made of a format for selecting the iso-degree-of-swirl line as the outer periphery of the secondary flow when the user designates the iso-degree-of-swirl line with the cursor (displays the designated iso-degree-of-swirl line with a dotted line), as shown in FIG. 20.

In addition, a format for the user to directly draw the image and for the input unit 21 to recognize may be used. In this way, a mode for the user to manually select the desired secondary flow may be shifted by the user operating a button or a switch prepared in a physical or software manner.

The determination condition setting unit 327 receives the content input by the user from the input unit 21 and determines the conditional expression for determining the secondary flow based on the input content. At this time, the coordinate of the representative point of the secondary flow candidate and the boundary line indicating the outer periphery of the secondary flow candidate input by the user designating with the cursor or drawing directly do not necessarily match the calculation result of the secondary flow candidate extraction unit 322.

In such a case, the representative point of the secondary flow candidate or the iso-degree-of-swirl line of the degree-of-swirl map close to the user input may be automatically re-selected. The boundary line of the secondary flow candidate may be changed according to the user input. The determination condition setting unit 327 determines the conditional expression for determining the secondary flow based on information on the representative point of the secondary flow candidate selected and the secondary flow candidate range based on the user input.

A specific method is, for example, to plot the secondary flow candidate in an image used for the determination by the user into an n-dimensional space with n feature amounts as an axis, and to determine a region where the determination can be made according to the determination result of the user. At that time, a function describing the region may be prepared in advance, and the coefficient may be determined by a method such as a least square method, based on the determination result of the user.

A plurality of functions may be prepared, and an optimum one may be selected therefrom. When the conditional expression that completely reproduces the determination result of the user cannot be obtained, a function that provides a closest determination result may be defined as the conditional expression for determining the secondary flow. Accordingly, the determination condition setting unit 327 generates the conditional expression for determining the secondary flow according to the secondary flow determination unit 324.

REFERENCE SIGN LIST

1 device main body
2 ultrasonic probe
3 living body
11 control unit
21 input unit
22 transmitting unit
23 receiving unit
24 display unit
25 memory
31 signal processing unit
32 secondary flow detection unit
311 B-mode image forming unit
312 velocity vector map calculation unit
313 display image forming unit
321 degree-of-swirl map calculation unit
322 secondary flow candidate extraction unit
323 feature amount calculation unit
324 secondary flow determination unit
325 secondary flow extraction unit
326 secondary flow image generation unit
327 determination condition setting unit
328 determination condition setting screen generation unit

The invention claimed is:

1. A secondary flow detection device, comprising:
a memory storing a program for secondary flow detection; and
a controller programmed to execute the program, causing the secondary flow detection device to:
obtain a velocity vector map calculated based on an echo signal reflected by an inspection target, calculate, as a value indicating a degree of a spatial change of a velocity vector, a degree of swirl based on the velocity vector map, and calculate, as a degree-of-swirl map, a spatial distribution of an iso-degree-of-swirl line obtained by connecting the degree of swirl indicating an equal value;
extract, as a secondary flow candidate, an iso-degree-of-swirl line satisfying a predetermined condition among the iso-degree-of-swirl line indicated in the degree-of-swirl map;
calculate a feature amount of the velocity vector inside the secondary flow candidate, wherein the feature amount comprises a distance between a first coordinate where a velocity in the velocity vector map is a minimum value and a second coordinate where the degree of swirl is a maximum value;
determine whether the secondary flow candidate is a desired secondary flow based on a score for the secondary flow candidate determined based on the feature amount and indicating a possibility that the secondary flow candidate is the desired secondary flow; and
extract and output the secondary flow candidate determined to be the desired secondary flow
wherein the controller calculates the feature amount based on the first coordinate of a point at which an absolute value of a velocity is minimum in the velocity vector map.

2. The secondary flow detection device according to claim 1, wherein the controller calculates the feature amount of the velocity vector at the outside of the secondary flow candidate.

3. The secondary flow detection device according to claim 1, wherein the feature amount is a quantitative value based on a shape of the iso-degree-of-swirl line indicating the secondary flow candidate, a coordinate of a representative point of the secondary flow candidate, or a velocity gradient.

4. The secondary flow detection device according to claim 1, wherein the controller calculates a vorticity as the degree of swirl and calculates, as the degree-of-swirl map, a spatial distribution of an iso-vorticity line obtained by connecting equal vorticity.

5. The secondary flow detection device according to claim 1, wherein a point where the degree of swirl takes an extreme value is extracted as a representative point of the secondary flow candidate in the degree-of-swirl map.

6. The secondary flow detection device according to claim 1, wherein the iso-degree-of-swirl line where the degree of swirl is equal to or greater than a predetermined threshold value is extracted as the secondary flow candidate in the degree-of-swirl map.

7. The secondary flow detection device according to claim 1, wherein the controller determines whether the secondary flow candidate is the desired secondary flow according to a condition input by a user.

8. The secondary flow detection device according to claim 1, wherein the controller determines a condition for determining whether the secondary flow candidate is the desired secondary flow for the velocity vector map.

9. The secondary flow detection device according to claim 1, wherein the controller determines a condition for determining whether the secondary flow candidate is the desired secondary flow automatically based on velocity information.

10. The secondary flow detection device according to claim 1, wherein the controller determines a condition for determining whether the secondary flow candidate is the desired secondary flow automatically based on information from an external device.

11. An ultrasonic signal processing device, comprising a secondary flow detection device according to claim 1.

12. The secondary flow detection device according to claim 1, wherein the secondary flow detection device outputs a scoring result of the score to a display screen.

13. The secondary flow detection device according to claim 12, wherein a color or a thickness of a representative point of the desired secondary flow varies depending on the score.

14. The secondary flow detection device according to claim 12, wherein the feature amount includes a plurality of feature amounts, and the display screen includes a separate tab for each of the plurality of feature amounts.

15. The secondary flow detection device according to claim 12, wherein the feature amount includes a plurality of feature amounts, and the display screen simultaneously displays all of the plurality of feature amounts for the secondary flow candidate.

16. The secondary flow detection device according to claim 1, wherein the feature amount includes a plurality of feature amounts, each of which has its own threshold value, and the desired secondary flow is determined based on at least three of the plurality of feature amounts.

17. A non-transitory computer-readable medium storing a secondary flow detection program causing a computer to execute:
- a degree-of-swirl map calculation step of obtaining a velocity vector map calculated based on an echo signal reflected by an inspection target, calculating, as a value indicating a degree of a spatial change of a velocity vector, a degree of swirl based on the velocity vector map, and calculating, as a degree-of-swirl map, a spatial distribution of an iso-degree-of-swirl line obtained by connecting the degree of swirl of an equal value;
- a secondary flow candidate extraction step of extracting, as a secondary flow candidate, an iso-degree-of-swirl line satisfying a predetermined condition among the iso-degree-of-swirl line indicated in the degree-of-swirl map;
- a feature amount calculation step of calculating a feature amount of the velocity vector inside the secondary flow candidate, wherein the feature amount comprises a distance between a first coordinate where a velocity in the velocity vector map is a minimum value and a second coordinate where the degree of swirl is a maximum value;
- a secondary flow determination step of determining whether the secondary flow candidate is a desired secondary flow based on a score for the secondary flow candidate determined based on the feature amount and indicating a possibility that the secondary flow candidate is the desired secondary flow; and
- a secondary flow extraction step of extracting and outputting the secondary flow candidate determined to be the desired secondary flow, wherein the controller calculates the feature amount based on the first coordinate of a point at which an absolute value of a velocity is minimum in the velocity vector map.

* * * * *